United States Patent
Ohuchi et al.

(10) Patent No.: US 10,039,524 B2
(45) Date of Patent: Aug. 7, 2018

(54) MEDICAL IMAGE DIAGNOSTIC APPARATUS AND MEDICAL IMAGING APPARATUS

(71) Applicant: TOSHIBA MEDICAL SYSTEMS CORPORATION, Otawara-shi (JP)

(72) Inventors: Hiroyuki Ohuchi, Kawasaki (JP); Koichiro Kurita, Nasushiobara (JP); Tomohisa Imamura, Kawasaki (JP); Satoshi Matsunaga, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 30 days.

(21) Appl. No.: 15/189,519

(22) Filed: Jun. 22, 2016

(65) Prior Publication Data
US 2017/0055953 A1    Mar. 2, 2017

(30) Foreign Application Priority Data

Aug. 27, 2015 (JP) .................. 2015-168226
May 23, 2016 (JP) .................. 2016-102358

(51) Int. Cl.
*G06F 3/041* (2006.01)
*A61B 8/00* (2006.01)
(Continued)

(52) U.S. Cl.
CPC ............ *A61B 8/469* (2013.01); *A61B 8/5207* (2013.01); *G06F 3/04883* (2013.01);
(Continued)

(58) Field of Classification Search
CPC ..... A61B 8/4444; A61B 8/4483; A61B 8/461; A61B 8/469; A61B 8/485; A61B 8/486;
(Continued)

(56) References Cited

U.S. PATENT DOCUMENTS

2013/0141362 A1* 6/2013 Asanuma ............... G06F 3/041
                                                      345/173
2014/0276057 A1* 9/2014 Lee ......................... A61B 8/469
                                                      600/441

FOREIGN PATENT DOCUMENTS

| JP | 2000-139914 | 5/2000 |
| JP | 2002-17685  | 1/2002 |
| JP | 2014-97127  | 5/2014 |

* cited by examiner

*Primary Examiner* — Insa Sadio
(74) *Attorney, Agent, or Firm* — Oblon, McClelland, Maier & Neustadt, L.L.P.

(57) ABSTRACT

A medical image diagnostic apparatus according to an embodiment includes image generation circuitry, a touch panel, and control circuitry. The image generation circuitry generates a medical image based on data collected through scanning on a subject. The touch panel displays the medical image, and detects a tap operation, a long-press operation, or a flick operation on the displayed medical image. The control circuitry changes a parameter that affects the display of the medical image in a region relative to a position where the tap operation, the long-press operation, or the flick operation is detected, based on at least one of the strength of the tap operation, the number of times of the tap operation, the strength of the long-press operation, the long-press time of the long-press operation, the strength of the flick operation, the direction of the flick operation, and the speed of the flick operation.

7 Claims, 13 Drawing Sheets

(51) Int. Cl.
*G06F 3/0488* (2013.01)
*A61B 8/08* (2006.01)

(52) U.S. Cl.
CPC ........... *A61B 8/4444* (2013.01); *A61B 8/4483* (2013.01); *A61B 8/461* (2013.01); *A61B 8/485* (2013.01); *A61B 8/486* (2013.01); *A61B 8/488* (2013.01); *A61B 8/5269* (2013.01); *A61B 8/54* (2013.01)

(58) Field of Classification Search
CPC ..... A61B 8/488; A61B 8/5207; A61B 8/5269; A61B 8/54; G06F 3/04883
See application file for complete search history.

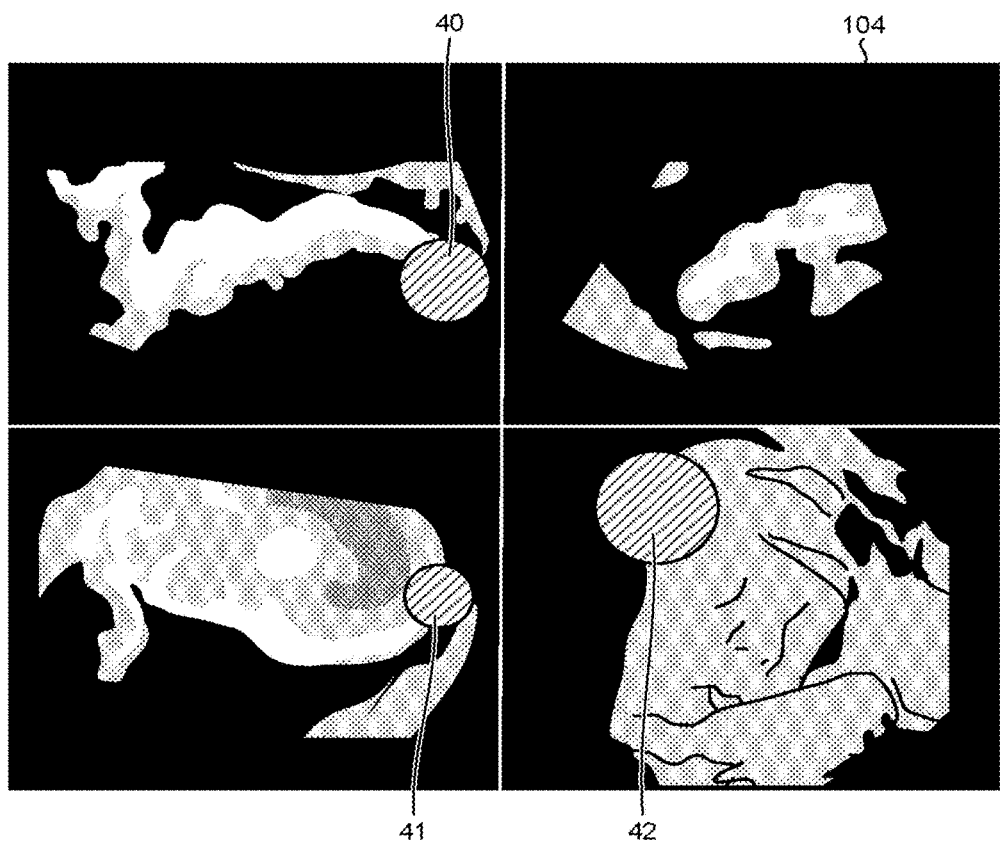

MEDICAL IMAGE DIAGNOSTIC APPARATUS AND MEDICAL IMAGING APPARATUS

CROSS-REFERENCE TO RELATED APPLICATIONS

This application is based upon and claims the benefit of priority from Japanese Patent Application No. 2015-168226, filed on Aug. 27, 2015; and Japanese Patent Application No. 2016-102358, filed on May 23, 2016, the entire contents of which are incorporated herein by reference.

FIELD

Embodiments described herein relate generally to a medical image diagnostic apparatus and a medical imaging apparatus.

BACKGROUND

Ultrasound transmitted from an ultrasound probe travels while being attenuated in a body, and thus a reflection signal reflected from a deeper region in the body is more likely to be attenuated. To equalize image quality, ultrasound diagnostic apparatuses are capable of previously setting various gains in a depth direction. However, the degree of the attenuation in fact differs among organs and persons, and thus varies for each inspection. Such ultrasound diagnostic apparatuses are capable of adjusting a gain in a time direction, that is, the depth direction. This function is referred to as sensitivity time control (STC) or time gain control (TGC).

Furthermore, image quality in an azimuthal direction may differ depending on how to place the ultrasound probe and a condition in the body of a subject. For example, this causes the left side of an ultrasound image to be dark. Thus, the ultrasound diagnostic apparatuses are capable of adjusting a gain in the azimuthal direction. This function is referred to as lateral gain control (LGC).

BRIEF DESCRIPTION OF THE DRAWINGS

FIGS. 9A and 9B illustrate processing of a touch panel and control circuitry according to a third embodiment;

DETAILED DESCRIPTION

A medical image diagnostic apparatus according to embodiments includes image-generating circuitry, a touch panel, and control circuitry. The image-generating circuitry generates a medical image based on data collected by scanning a subject. The touch panel displays the medical image and detects a tap operation, a long-press operation, or a flick operation on the displayed medical image. The control circuitry changes a parameter that affects the display of the medical image in a region relative to a position where the tap operation, the long-press operation, or the flick operation is detected, based on at least one of the strength of the tap operation, the number of times of the tap operation, the strength of the long-press operation, the long-press time of the long-press operation, the strength of the flick operation, the direction of the flick operation, and the speed of the flick operation.

The medical image diagnostic apparatus and a medical imaging apparatus according to the embodiments will now be described with reference to the drawings. Hereinafter, an ultrasound diagnostic apparatus will be described as an example of the medical image diagnostic apparatus according to the embodiments, but embodiments are not limited thereto. For example, the medical image diagnostic apparatus according to the embodiments is not limited to the ultrasound diagnostic apparatus, and may be a medical image diagnostic apparatus, such as an x-ray diagnostic apparatus, an x-ray computed tomography (CT) apparatus, a magnetic resonance imaging (MRI) apparatus, a single photon emission computed tomography (SPECT) apparatus, a positron emission computed tomography (PET) apparatus, a SPECT-CT apparatus that is a combination of the SPECT apparatus and the x-ray CT apparatus, a PET-CT apparatus that is a combination of the PET apparatus and the x-ray CT apparatus, and a subject testing apparatus. Furthermore, the medical image diagnostic apparatus according to the embodiments is not limited to a medical image diagnostic apparatus, and may be a medical imaging apparatus that performs predetermined processing (work) on a medical image or an image display apparatus that displays a medical image.

First Embodiment

Figure 1:
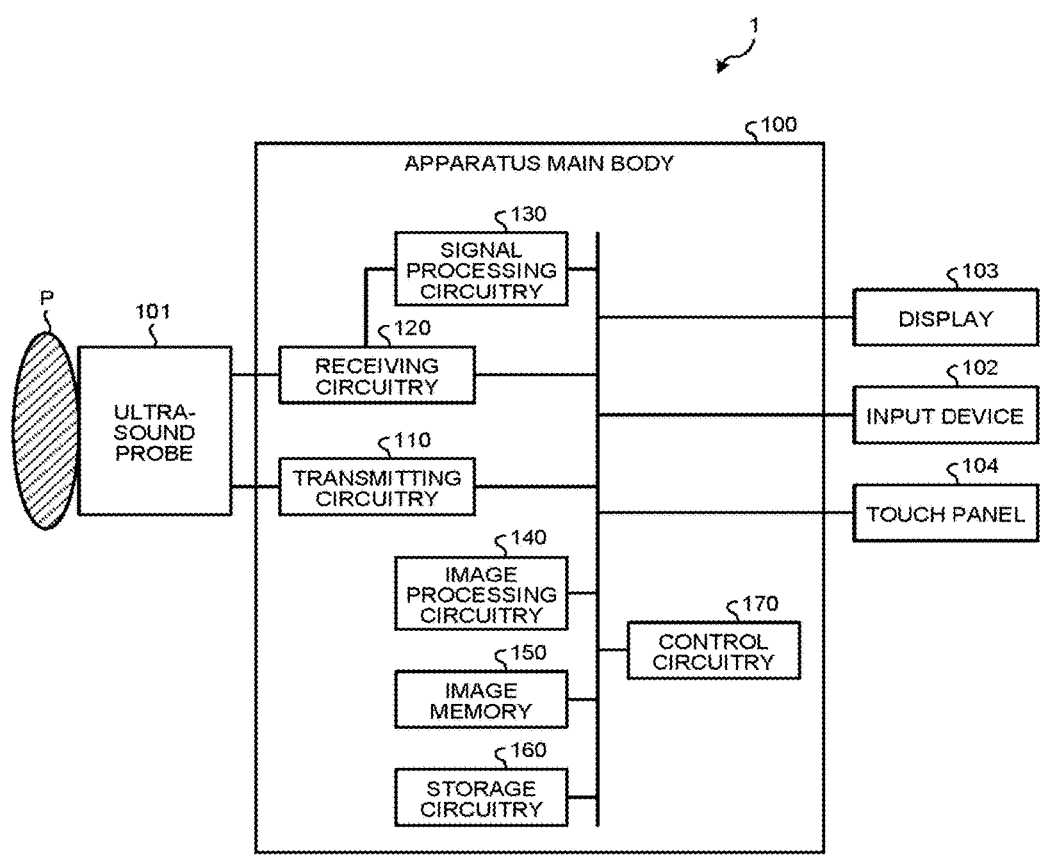
FIG. 1 is a block diagram illustrating an example configuration of an ultrasound diagnostic apparatus according to a first embodiment.

FIG. 1 is a block diagram illustrating an example configuration of an ultrasound diagnostic apparatus 1 according to a first embodiment. As illustrated in FIG. 1, the ultrasound diagnostic apparatus 1 according to the first embodiment includes an apparatus main body 100, an ultrasound probe 101, an input device 102, a display 103, and a touch panel 104. The ultrasound probe 101, the input device 102, the display 103, and the touch panel 104 are each coupled to the apparatus main body 100.

The ultrasound probe 101 is placed on the body surface of a subject P, and performs ultrasound transmission and reception (ultrasound scanning). For example, the ultrasound probe 101 is a 1D array probe (search unit) that has a plurality of piezoelectric transducer elements arranged one-dimensionally in a predetermined direction. The piezoelectric transducer elements generate ultrasound based on driving signals supplied by transmitting circuitry 110 described below, which is included in the apparatus main body 100.

The generated ultrasound is reflected on surfaces having mismatched acoustic impedances in the body of the subject P, and is received as reflected-wave signals including components scattered by scatterers in tissues, by the piezoelectric transducer elements. The ultrasound probe 101 sends the reflected-wave signals received by the piezoelectric transducer elements to receiving circuitry 120.

In this embodiment, it will be described that the 1D array probe is used as the ultrasound probe 101, but the embodiment is not limited thereto. For example, the ultrasound probe 101 may be any type of ultrasound probe, such as a 2D array probe in which a plurality of piezoelectric transducer elements are arranged two-dimensionally in a grid pattern and a mechanical 4D probe in which a plurality of piezoelectric transducer elements arranged one-dimensionally oscillate mechanically to scan a three-dimensional region.

Examples of the input device 102 include a mouse, a keyboard, a button, a panel switch, a touch command screen, a foot switch, a trackball, and a joystick. The input device 102 receives various kinds of setting requests from an operator of the ultrasound diagnostic apparatus 1, and transfers the various kinds of received setting requests to the apparatus main body 100.

The display 103 displays a graphical user interface (GUI) used by the operator of the ultrasound diagnostic apparatus 1 to input various kinds of setting requests with the input device 102, and displays ultrasound image data generated in the apparatus main body 100 and other data.

The touch panel 104 is a device that displays a medical image and detects a touch operation on the displayed medical image. For example, the touch panel 104 receives touch operations including operations such as a tap operation, a long-press operation, and a slide operation. In other words, the touch panel 104 is a device that displays a medical image and detects a tap operation or a long-press operation on the displayed medical image. Specifically, as the content of the touch operation, the touch panel 104 detects information, such as a position (coordinates) touched through the touch operation by an operator, a time for which the operator is in contact with the position, and the number of times of the touching, and outputs the detected information to the apparatus main body 100. The touch operation may be performed using a tool including a stylus, without any direct touching by the operator.

The apparatus main body 100 is an apparatus that generates ultrasound image data based on reflected-wave signals received by the ultrasound probe 101. As illustrated in FIG. 1, the apparatus main body 100 includes, for example, the transmitting circuitry 110, the receiving circuitry 120, signal processing circuitry 130, image processing circuitry 140, an image memory 150, storage circuitry 160, and control circuitry 170. The transmitting circuitry 110, the signal processing circuitry 130, the image processing circuitry 140, the image memory 150, the storage circuitry 160, and the control circuitry 170 are communicatively coupled to each other.

The transmitting circuitry 110 controls ultrasound transmission from the ultrasound probe 101. For example, the transmitting circuitry 110 includes a trigger-generating circuit, a transmission-delaying circuit, and a pulser circuit, and supplies driving signals to the ultrasound probe 101. The pulser circuit repeatedly generates rate pulses for forming transmitted ultrasound, at a predetermined rate frequency. Furthermore, the transmission-delaying circuit gives a delay time for each piezoelectric transducer element to the corresponding rate pulse generated by the pulser circuit. Such a delay time is required to converge ultrasound generated by the ultrasound probe 101 into a beam and determine transmission directionality. Furthermore, the trigger-generating circuit supplies the driving signals (driving pulses) to the ultrasound probe 101 at a timing based on the rate pulses. That is, the transmission-delaying circuit desirably adjusts a transmission direction from the surface of the piezoelectric transducer elements by varying the delay time given to each rate pulse.

The transmitted ultrasound is reflected by tissues in the body to be reflected-wave signals, and the receiving circuitry 120 controls receiving such reflected-wave signals. For example, the receiving circuitry 120 includes an amplifying circuit, an analog to digital (A/D) converter, an adder, and a phase-detecting circuit, and performs various types of processing on the reflected-wave signals received by the ultrasound probe 101 to generate reflected-wave data. The amplifying circuit amplifies the reflected-wave signals for each channel to perform gain-correction processing. The A/D converter performs A/D conversion of the gain-corrected reflected-wave signals and gives a delay time required to determine reception directivity to the resulting digital data. The adder performs addition processing of the reflected-wave signals processed by the A/D converter. The addition processing performed by the adder enhances a reflection component from the direction corresponding to the reception directivity of the reflected-wave signals. The phase-detecting circuit converts an output signal from the adder into an in-phase signal (I signal) and a quadrature-phase signal (Q signal) in a baseband. The phase-detecting circuit then outputs the I signal and Q signal (IQ signal) to the subsequent signal processing circuitry 130. Data before the processing of the phase-detecting circuit is also referred to as an RF signal. Hereinafter, the "IQ signal" and the "RF signal" generated based on reflected waves of ultrasound are collectively described as "reflected-wave data".

The signal processing circuitry 130 performs various types of signal processing on reflected-wave data that the receiving circuitry 120 generates from the reflected-wave signals. For example, the signal processing circuitry 130 receives the reflected-wave data from the receiving circuitry 120, performs logarithmic amplification, envelope detection processing, and other processing on the received data, and generates data (B-mode data) in which signal intensity is represented by the brightness of luminance. Furthermore, the signal processing circuitry 130 performs frequency analysis of velocity information from the reflected-wave data received by the receiving circuitry 120, extracts an echo component from a blood stream, a tissue, and a contrast agent due to the Doppler effect, and generates data (Doppler data) in which moving-object information, including an average velocity, dispersion, and a power, is extracted at many points.

The signal processing circuitry 130 is capable of processing of both two-dimensional reflected-wave data and three-dimensional reflected-wave data. That is, the signal processing circuitry 130 generates two-dimensional B-mode data from two-dimensional reflected-wave data and generates three-dimensional B-mode data from three-dimensional reflected-wave data. Furthermore, the signal processing circuitry 130 generates two-dimensional Doppler data from two-dimensional reflected-wave data and generates three-dimensional Doppler data from three-dimensional reflected-wave data.

The image processing circuitry 140 generates ultrasound image data from data generated by the signal processing circuitry 130 and performs various types of image processing on the generated ultrasound image data. That is, the image processing circuitry 140 generates B-mode image data from B-mode data. Such B-mode image data represents the intensity of reflected waves as luminance. Furthermore, the image processing circuitry 140 generates Doppler image data from Doppler data. Such Doppler image data is an average velocity image, a dispersion image, a power image, or a combination image thereof that represents moving-object information. Furthermore, the image processing circuitry 140 can generate a combined image that is a combination of an ultrasound image with, for example, text information of various parameters, scales, and body marks. The image processing circuitry 140 is an example of an image-generating unit that generates a medical image based on data collected by scanning a subject.

The image processing circuitry 140 converts (scan-converts) a scanning line signal column of ultrasound scanning into a scanning line signal column of the video format represented by a television system, to thereby generate ultrasound image data serving as a display image. Furthermore, the image processing circuitry 140 performs various kinds of image processing in addition to scan-conversion, such as image processing (smoothing processing) for regenerating a luminance average value image by using a plurality of image frames after scan-conversion, and image processing (edge enhancement processing) using a differential filter within an image.

In other words, the B-mode data and the Doppler data are ultrasound image data before scan-conversion processing, and the data generated by the image processing circuitry 140 is display ultrasound image data after scan-conversion processing.

Furthermore, the image processing circuitry 140 performs rendering of volume data, to generate various types of two-dimensional image data for displaying the volume data on the display 103 and the touch panel 104. An example of the rendering performed by the image processing circuitry 140 is processing that generates multi planar reconstruction (MPR) image data from volume data using an MPR method. Another example of the rendering performed by the image processing circuitry 140 is processing that performs "Curved MPR" on volume data and processing that performs "Intensity Projection" on volume data. Still another example of the rendering performed by the image processing circuitry 140 is volume rendering (VR) that generates two-dimensional image data reflecting three-dimensional information.

The image memory 150 is a memory configured to store therein image data generated by the image processing circuitry 140. Furthermore, the image memory 150 is capable of storing therein data generated by the signal processing circuitry 130. The data stored in the image memory 150 can be invoked by the operator after diagnosis, for example, and serve as display ultrasound image data via the image processing circuitry 140.

The storage circuitry 160 stores therein control programs for executing ultrasound transmission and reception, image processing, and display processing; diagnosis information (for example, patient IDs and doctor's findings); and various kinds of data such as diagnosis protocols and various kinds of body marks. If necessary, the storage circuitry 160 is also used to store therein image data stored in the image memory 150. Furthermore, the data stored in the storage circuitry 160 can be transferred to an external device via an interface unit (not illustrated).

The control circuitry 170 controls the overall processing of the ultrasound diagnostic apparatus 1. Specifically, the control circuitry 170 controls processing of the transmitting circuitry 110, the receiving circuitry 120, the signal processing circuitry 130, the image processing circuitry 140, and other circuits, based on various types of setting requests input by the operator via the input device 102 and the touch panel 104, and various types of control programs and data read from the storage circuitry 160. Furthermore, the control circuitry 170 displays ultrasound image data stored in the image memory 150 on the display 103.

The image processing circuitry 140 and the control circuitry 170 according to the first embodiment perform processing functions described in this embodiment. The processing functions performed by the image processing circuitry 140 and the control circuitry 170 are stored in the storage circuitry 160, for example, in the form of computer programs executable by computers. The image processing circuitry 140 and the control circuitry 170 are processors that read each computer program from the storage circuitry 160 and execute it to implement the function corresponding to each computer program. In other words, after reading each computer program, the image processing circuitry 140 and the control circuitry 170 have the respective processing functions. The processing functions of the image processing circuitry 140 and the control circuitry 170 will be discussed below.

Such functions of the image processing circuitry 140 and the control circuitry 170 may be implemented by using a configuration in which several independent processors are combined into a processing circuit and each processor executes the corresponding computer program.

The term "processor" used in the above description means, for example, a central processing unit (CPU), a graphics processing unit (GPU), or a circuit such as an application specific integrated circuit (ASIC), a programmable logic device (for example, a simple programmable logic device (SPLD), a complex programmable logic device (CPLD), and a field programmable gate array (FPGA)). The processor implements its functions by reading and executing the programs stored in the storage circuit. Note that a computer program may be directly incorporated in a circuit of the processor instead of storing a computer program in the storage circuitry 160. In this case, the processor implements its functions by reading and executing the programs incorporated in the circuit. Note that each processor in this embodiment is not limited to the case where each processor is configured as a single circuit, and a plurality of independent circuits may be combined to configure a single processor so as to implement their functions. In addition, the components in FIG. 1 may be integrated into a single processor so as to implement their functions.

Time gain control (TGC) and lateral gain control (LGC) will be described. The TGC adjusts a gain in a depth direction and the LGC adjusts a gain in an azimuthal direction.

Figure 2:
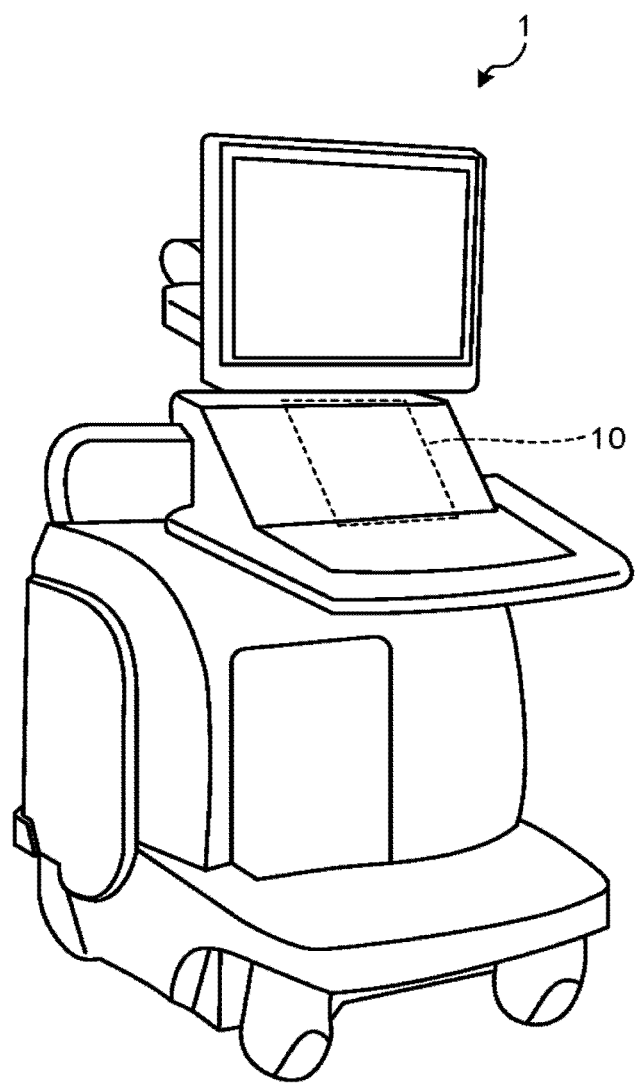
FIG. 2 is a diagram illustrating the TGC and the LGC.
Figure 3:
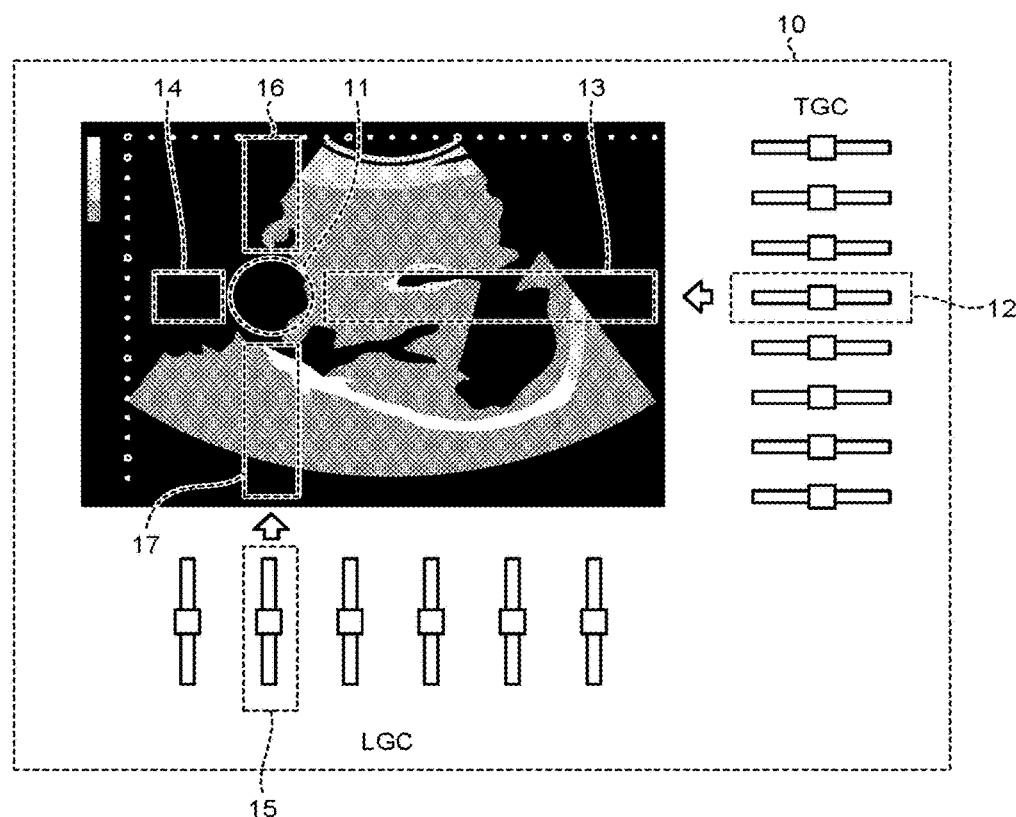
FIG. 3 is a diagram illustrating the TGC and the LGC.

FIGS. 2 and 3 are diagrams illustrating the TGC and the LGC. FIG. 2 illustrates a location where the TGC and the LGC are installed, in the ultrasound diagnostic apparatus 1. Furthermore, FIG. 3 illustrates gain control using the TGC and the LGC. As illustrated in FIG. 2, the TGC and the LGC are placed on an operating panel 10 of the ultrasound diagnostic apparatus 1.

As illustrated in FIG. 3, the TGC and the LGC each have several knobs, and the brightness of an ultrasound image is partially changed by moving such knobs individually. For example, the TGC has eight knobs in a vertical direction. Each of the eight knobs corresponds to each region obtained by dividing an ultrasound image into eight equal parts in the depth direction. The LGC has six knobs in a lateral direction.

Each of the six knobs corresponds to each region obtained by dividing an ultrasound image into six equal parts in the azimuthal direction.

In FIG. 3, it will be described that the range of a region 11 of the ultrasound image is brightened. In this case, the operator performs moving a fourth knob 12 from the top of the TGC right, moving a second knob 15 from the left of the LGC upward, or a combination thereof. Such operations brighten the region 11, whereas the operations also affect a region other than the region 11. Specifically, moving the knob 12 right also brightens regions 13 and 14 in the same depth as the region 11. Furthermore, moving the knob 15 upward also brightens regions 16 and 17 in the same azimuth as the region 11.

In this way, for operations of the TGC and the LGC, when the operator adjusts the brightness of a desired region, regions other than the desired region are also affected. Thus, for example, the change of the brightness in regions having originally appropriate brightness may affect a diagnosis. That is, operations of the TGC and the LGC may be unusable to change the brightness of the desired region. The above description is made for the brightness of an image, but is not limited to this. This description is widely common in changing parameters that affect the display of images, such as image processing filters, frequencies, and dynamic ranges.

To easily change the image quality of a desired region, the ultrasound diagnostic apparatus 1 according to the embodiment includes the disclosed configuration.

The touch panel 104 displays a medical image, and detects a touch operation on the displayed medical image. For example, the touch panel 104 is installed on an operation panel 10 of the ultrasound diagnostic apparatus 1, and displays an ultrasound image generated by the image processing circuitry 140. The touch panel 104 then receives indication of a position (coordinates) where the operator performs a touch operation (a touch on the image), in the displayed ultrasound image. The touch panel 104 need not be installed on the operation panel. For example, the touch panel 104 may be installed as a sub display adjacent to the display 103, or may be installed as a main display in combination with the display 103. The touch panel 104 may be also installed with a separate enclosure, as an external device for the ultrasound diagnostic apparatus 1.

Figure 4:
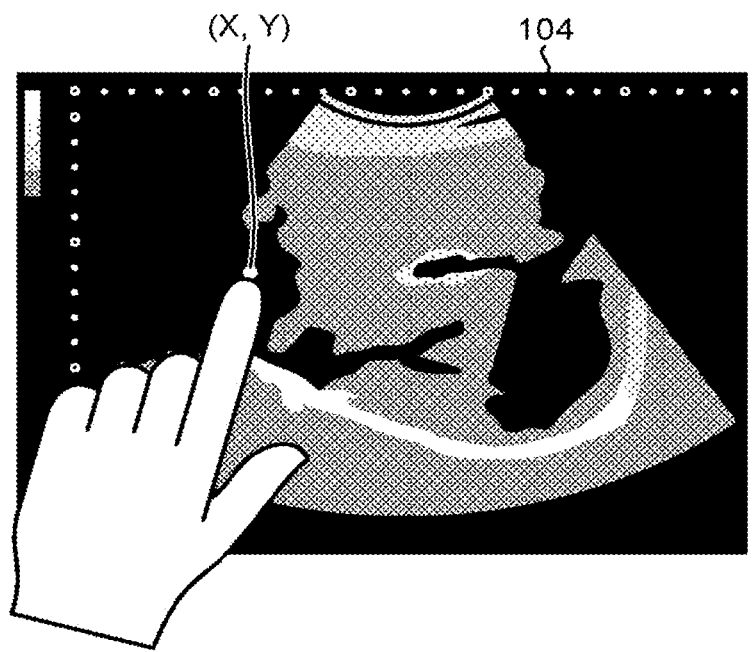
FIG. 4 is a diagram illustrating processing of a touch panel according to the first embodiment.

FIG. 4 is a diagram illustrating processing of the touch panel 104 according to the first embodiment. FIG. 4 illustrates the touch panel 104 that displays an ultrasound image. As illustrated in FIG. 4, the touch panel 104 detects a touch operation from the operator. Specifically, when the operator taps a single point on the touch panel 104, the touch panel 104 detects the coordinates (X, Y) of the tapped position. The touch panel 104 then outputs the detected coordinates (X, Y) to the control circuitry 170.

FIG. 4 is only by way of example, and the touch panel 104, for example, may receive any touch operation other than tapping. For example, the touch panel 104 receives operations, such as long-pressing and sliding, as touch operations other than tapping. When receiving long-pressing, the touch panel 104 outputs a position (coordinates) indicated by the operator as well as a time for long pressing the position. When receiving sliding, the touch panel 104 outputs the coordinates of a plurality of positions traced by the sliding. For example, when receiving tapping multiple times, the touch panel 104 can also output the number of times of the tapping.

The control circuitry 170 changes a parameter that affects the display of a medical image in a region relative to a position where a tap operation or a long-press operation is detected. For example, the control circuitry 170 changes a parameter that affects the display of a medical image in a region relative to a position where a tap operation or a long-press operation is detected, based on the number of times of the tap operation or a long-press time of the long-press operation.

For example, the control circuitry 170 changes a parameter in a region including a position where a touch operation is detected. Specifically, the control circuitry 170 changes a parameter in a square region, a cubic region, a circle region, or a sphere region including a position where a tap operation or a long-press operation is detected.

Figure 5A:
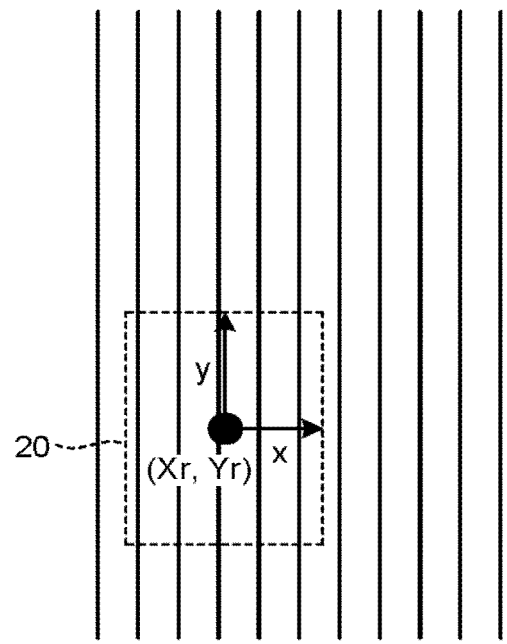
FIGS. 5A to 5D are diagrams illustrating processing of control circuitry according to the first embodiment.
Figure 5B:
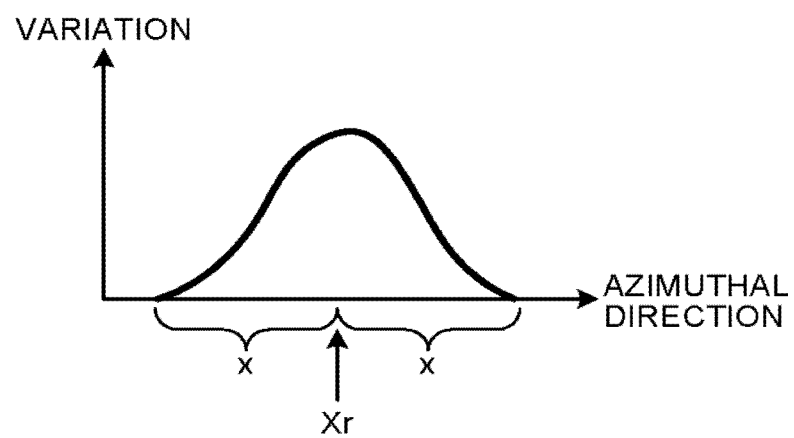
Figure 5C:
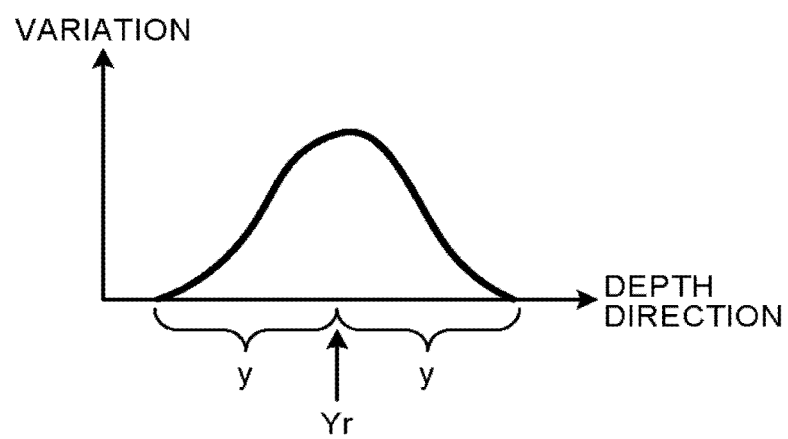
Figure 5D:
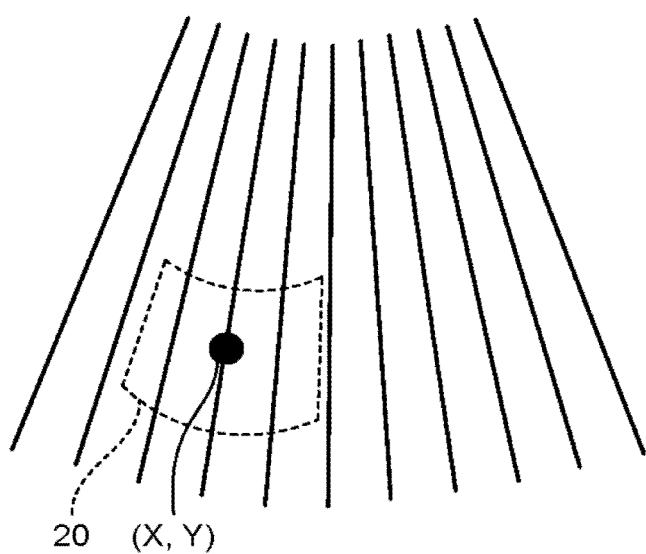

FIGS. 5A to 5D are diagrams illustrating processing of the control circuitry 170 according to the first embodiment. FIG. 5A illustrates a plurality of scan lines in raw data (before scan conversion). Furthermore, FIGS. 5B and 5C illustrate the variation of a gain as a function of a distance from a reference (reference point). In FIGS. 5B and 5C, horizontal axes indicate a position (the azimuthal direction and the depth direction, respectively), and longitudinal axes indicate the variation. FIG. 5D illustrates a plurality of scan lines in an ultrasound image (after scan conversion). In FIGS. 5A to 5D, it will be described that the touch panel 104 is tapped at the position of the coordinates (X, Y) one time.

As illustrated in FIG. 5A, upon receiving the coordinates (X, Y) output by the touch panel 104, the control circuitry 170 calculates coordinates (Xr, Yr) on the raw data corresponding to the coordinates (X, Y). The control circuitry 170 then determines a rectangular region 20 having the calculated coordinates (Xr, Yr) at its center (reference point) to be a region in which a parameter is to be changed. In this example, the control circuitry 170 determines the rectangular region 20 having the coordinates (Xr, Yr) at its center and included in x in each of the left and the light directions and included in y in each of the up and down directions to be a region in which a parameter is to be changed. The size of the rectangular region 20 is set in advance by the operator and is registered in the storage circuitry 160, for example.

As illustrated in FIG. 5B and FIG. 5C, the control circuitry 170 determines the variation of the parameter depending on the distance from the reference (reference point). For example, the control circuitry 170 determines a smaller variation for the gain as the distance from the reference point (Xr) increases in the azimuthal direction. The control circuitry 170 determines a smaller variation for the gain as the distance from the reference point (Yr) increases also in the depth direction. The variation of the gain is set in advance by the operator and is registered in the storage circuitry 160, for example.

The control circuitry 170 changes the gain corresponding to each sample point included in the determined rectangular region 20 in accordance with the determined variation. For example, the control circuitry 170 changes the gain of gain-correction processing performed by the receiving circuitry 120 for each sample point in accordance with the determined variation. Specifically, the control circuitry 170 changes the gain of each sample point registered in the receiving circuitry 120 in accordance with the determined variation.

Subsequently, gain is changed in the rectangular region 20 having the coordinates (X, Y) at its center in a generated ultrasound image. The shape of the rectangular region 20 in the ultrasound image is warped due to scan conversion (refer to FIG. 5D). With this shape, parameters of sample points with the same depth direction are to be changed; therefore, this is suitable for the characteristics of ultrasound image diagnoses, in which reflection signals are likely to attenuate in the depth direction.

In this manner, the control circuitry 170 changes a parameter in a region based on the position of the touch operation. Note that FIG. 5A to FIG. 5D are only illustrative. For example, the shape of the region in which a parameter is to be changed is not limited to rectangular (for example, a square region), and can be set as appropriate to circular (for example, a circle region) or elliptic, for example. The shape of the region in which a parameter is to be changed is set on the raw data before scan conversion in this example; however, this is not limiting and the shape can be set on an ultrasound image after scan conversion, for example. Because reflection signals are likely to attenuate in the depth direction in ultrasound image diagnoses, this shape is preferably set in accordance with the shape of a contact point between the ultrasound probe 101 and the subject, for example. The variation of a parameter depending on the distance from the reference is not limited to following a curved line (S-letter variation) as illustrated in FIG. 5B and FIG. 5C, but may be linear or constant irrespective of the distance.

Furthermore, a description is given of the case where the parameters related to raw data are changed in the example described above, but embodiments are not limited to this. For example, parameters related to IQ signals (IQ data) may be changed. In this case, for example, parameters such as reception frequency are adjustable. This makes it possible to locally set image quality for high frequencies, and this is suitable for a case where a tumor site in an image needs to be observed in higher image quality, for example. Parameters of an ultrasound image after scan conversion may also be changed.

Furthermore, a description is given of the case where the touch panel 104 receives a single tap in the example described above, but embodiments are not limited to this. For example, upon receiving multiple taps, the control circuitry 170 may change parameters depending on the number of taps having been made. Upon receiving long press, the control circuitry 170 may change parameters depending on the time for which the long press has been made. With this configuration, for example, as the time during which the operator is making a long tap is extended, the luminance of the image in the region with the contact point serving as the reference point increases. In this case, the ratio of an increase in the gain to the contact time may be set by the user. Alternatively, the luminance of the image may be set to decrease as the contact time is extended.

Figure 6:
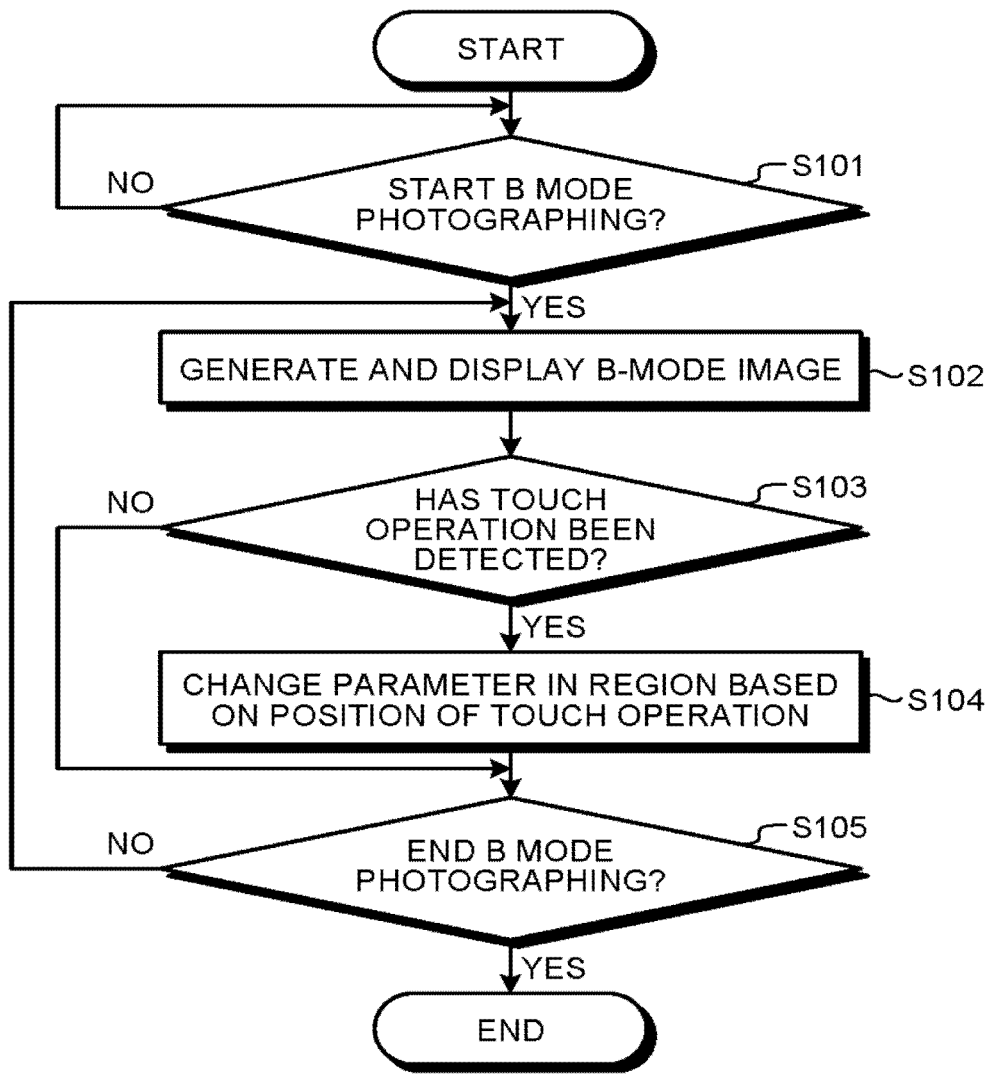
FIG. 6 is a flowchart illustrating a process of the ultrasound diagnostic apparatus according to the first embodiment.

FIG. 6 is a flowchart illustrating a process of the ultrasound diagnostic apparatus 1 according to the first embodiment. The processing illustrated in FIG. 6 starts with reception of an instruction to start B mode photographing from the operator while the ultrasound probe 101 is brought in contact with the body surface of the subject P, for example.

At Step S101, the ultrasound diagnostic apparatus 1 determines whether to start B mode photographing. For example, the control circuitry 170 starts B mode photographing upon receiving an instruction to start B mode photographing from the operator. Note that when the determination at Step S101 is negative, the control circuitry 170 remains in a standby state without starting photographing.

When the determination at Step S101 is positive, at Step S102, the ultrasound diagnostic apparatus 1 generates a B-mode image and displays the image on the touch panel 104.

At Step S103, the touch panel 104 determines whether it has detected a touch operation. For example, upon detecting a touch operation, the touch panel 104 outputs coordinates specified by the detected touch operation to the control circuitry 170. When the determination at Step S103 is negative, the process of the control circuitry 170 proceeds to the processing at Step S105.

When the determination at Step S103 is positive, at Step S104, the control circuitry 170 changes a parameter in a region based on the position of the touch operation. For example, the control circuitry 170 determines the rectangular region 20 centering on the tapped position as a region where a parameter is changed. The control circuitry 170 then determines the variation of the parameter depending on the distance from the reference (reference point). The control circuitry 170 changes the gain corresponding to each sample point included in the determined rectangular region 20 depending on the determined variation.

At Step S105, the control circuitry 170 determines whether an instruction to end the B mode photographing has been received from the operator. In this example, when the determination at Step S105 is negative, the process of the control circuitry 170 proceeds to the processing at Step S102. In other words, the ultrasound diagnostic apparatus 1 performs ultrasound scanning on the next frame, and generates and displays a B-mode image of the next frame.

For example, when the determination at Step S105 is positive, the ultrasound diagnostic apparatus 1 ends the processing of B mode photographing. Note that FIG. 6 is only illustrative. For example, the processing described above is not necessarily performed in the above-described order. For example, Steps S101 to S105 described above may be performed in another order as long as the specified processing can be satisfactorily performed.

As described above, in the ultrasound diagnostic apparatus 1 according to the first embodiment, the touch panel 104 displays a medical image, and detects a touch operation on the displayed medical image. The control circuitry 170 changes a parameter that affects the display of the medical image in a region relative to a position where the touch operation is detected. With this configuration, the ultrasound diagnostic apparatus 1 can easily change the image quality of a desired region.

Modifications of First Embodiment

A description is given of the case where the parameter is changed depending on a value set in advance, in other words, the parameter is increased or decrease in the first embodiment, but embodiments are not limited to this. For example, the ultrasound diagnostic apparatus 1 may change the parameter through a touch operation after allowing the operator to select whether to increase or decrease the parameter.

Figure 7:
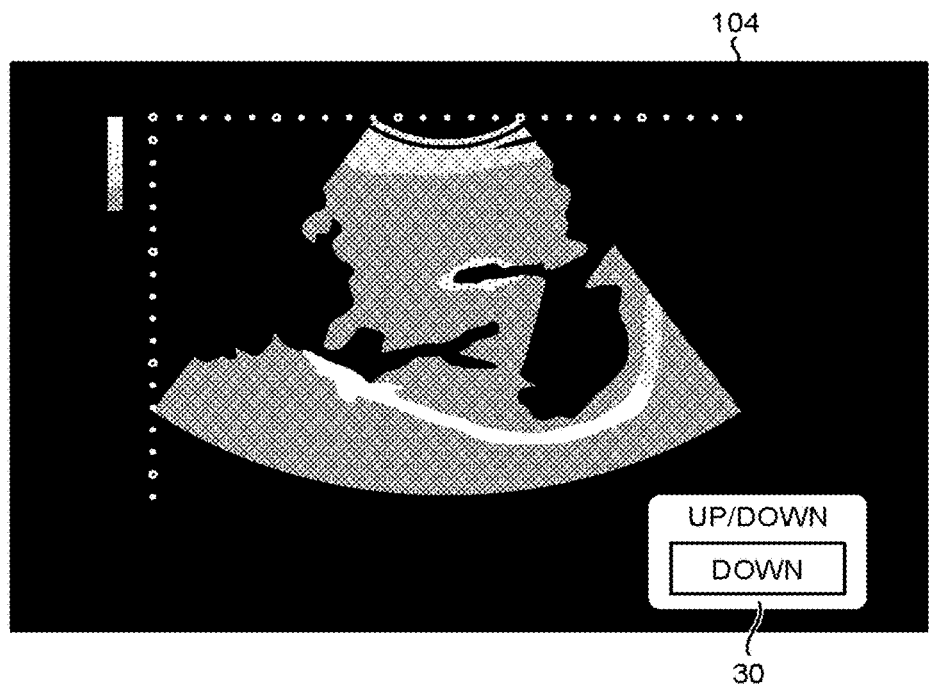
FIG. 7 is a diagram illustrating processing of a touch panel and control circuitry according to a modification of the first embodiment.

FIG. 7 is a diagram illustrating processing of the touch panel 104 and the control circuitry 170 according to a modification of the first embodiment. The touch panel 104 illustrated in FIG. 7 displays a GUI 30 for allowing selection to increase or decrease parameters on an ultrasound image. The GUI 30 illustrated in FIG. 7 currently displays "Down". This display "Down" indicates a decrease in a certain parameter when the touch panel 104 receives a touch operation in this state.

As illustrated in FIG. 7, the touch panel 104 displays the GUI 30. In this example, the display "Down" is switched to "Up" in response to a tap on the GUI 30 made by the operator. The display "Up" indicates an increase in a certain parameter when the touch panel 104 receives a touch operation in this state.

Specifically, the touch panel 104 displays a graphic for allowing a determination on whether to increase or decrease the parameter, and detects a touch operation on the displayed graphic. The control circuitry 170 then changes setting on whether to increase or decrease the parameter based on the touch operation on the medical image, depending on the touch operation detected on the graphic. With this configuration, the operator can change the parameter through the touch operation after selecting whether to increase or decrease the parameter.

The GUI displayed on the touch panel 104 is not limited to the GUI 30 described above. For example, the touch panel 104 may display an "Undo" button for undoing the last operation. This is useful when the operator needs to cancel the last action that increases the gain excessively, for example.

Furthermore, the touch panel 104 may display a "Reset" button for restoring the change history of parameters to its initial state. This is useful for changing a field of view (operational range), for example. For example, in a case where a tomographic image of a liver is observed with a part of the gain of the ultrasound image enhanced and a kidney is observed thereafter, the change history of the parameter that was changed before the observation of the liver would be unnecessary. In this case, pressing the "Reset" button one time restores the change in the parameter set for the observation of the liver to the initial setting, so that a tomographic image of the kidney can be rendered in the initial setting.

Second Embodiment

While the first embodiment describes a case of changing a parameter in a region including the position where a touch operation is detected, embodiments are not limited to this. For example, the ultrasound diagnostic apparatus 1 may change a parameter in a region defined by a plurality of positions specified by a touch operation.

The ultrasound diagnostic apparatus 1 according to a second embodiment includes almost the same configuration as that of the ultrasound diagnostic apparatus 1 illustrated in FIG. 1, and differs therefrom in part of the processing performed by the control unit 170. The second embodiment will mainly describe differences from the first embodiment and omit descriptions on the components that have the same functions as those described in the first embodiment.

Figure 8:
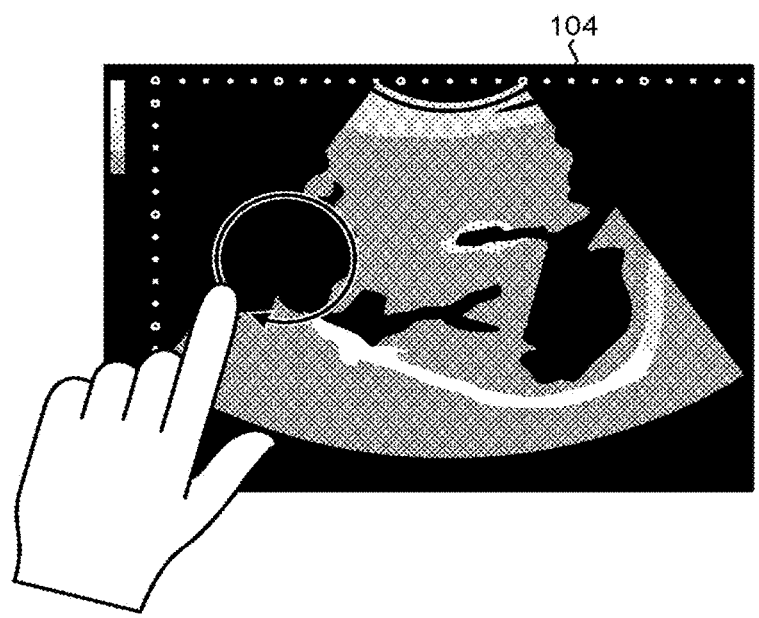
FIG. 8 is a diagram illustrating processing of control circuitry according to a second embodiment.

FIG. 8 is a diagram illustrating processing of the control circuitry 170 according to the second embodiment. The arrow in FIG. 8 indicates the trajectory of a touch operation made by the operator on the touch panel 104.

As illustrated in FIG. 8, while the operator is performing a touch operation tracing a circle on the touch panel 104, the touch panel 104 sequentially detects coordinates of a plurality of positions on the traced trajectory. The touch panel 104 outputs the detected coordinates to the control circuitry 170.

When the touch panel 104 detects a touch operation specifying a plurality of positions, the control circuitry 170 changes a parameter in a region defined by the detected positions. Specifically, the control circuitry 170 changes a parameter in the region defined by the arrow in FIG. 8. This configuration allows the operator to change parameters in a region of a desired shape.

Third Embodiment

While the embodiments described above describe a case of changing a parameter in two-dimensional ultrasound image data, embodiments are not limited to this. For example, the ultrasound diagnostic apparatus 1 may change a parameter in three-dimensional ultrasound image data.

Figure 9A:
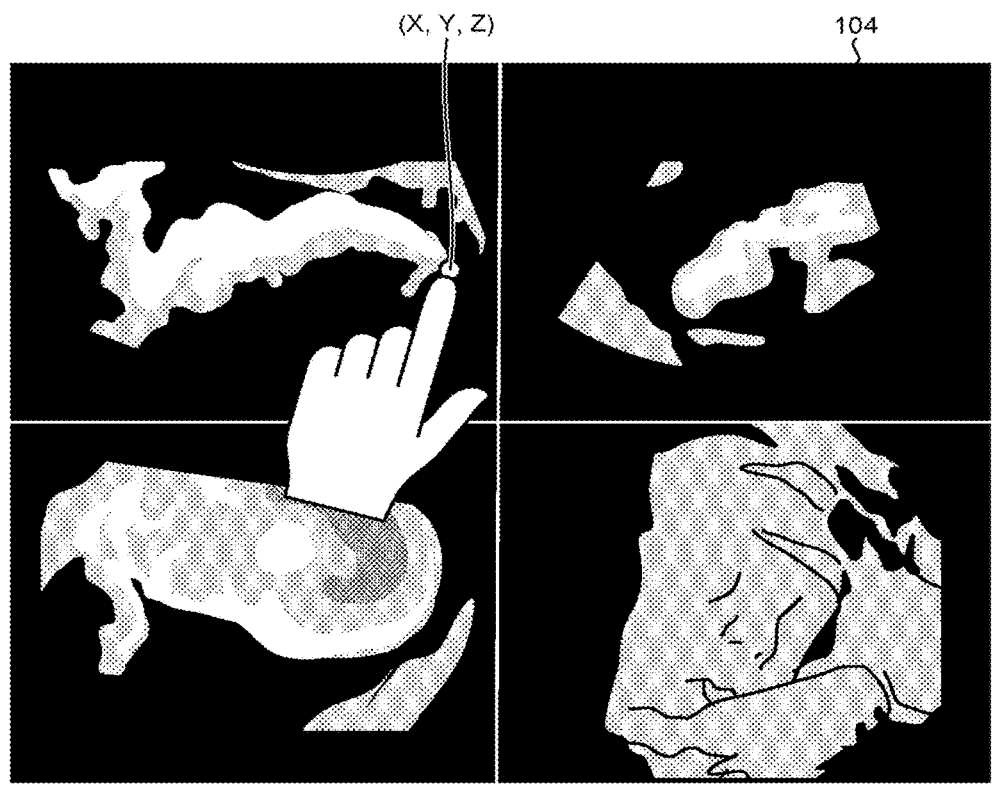

FIGS. 9A and 9B are diagrams illustrating processing of a touch panel 104 and a control circuitry 170 according to a third embodiment. In FIG. 9A and FIG. 9B, the images on the lower right are images obtained through VR processing of volume data in which a state of a fetus is rendered. The images on the upper right, the upper left, and the lower left are tomographic images of the volume data in the x, the y, and the z directions, respectively.

As illustrated in FIG. 9A, for example, the touch panel 104 detects coordinates (X, Y, Z) in the volume data through a tap on the tomographic images. The touch panel 104 then outputs the detected coordinates (X, Y, Z) to the control circuitry 170.

The control circuitry 170 then changes a certain parameter in a region relative to the coordinates (X, Y, Z) output by the touch panel 104. With this operation, as illustrated in FIG. 9B, images with parameters changed in regions 40, 41, and 42 are displayed. When a region with a parameter changed is not included in a tomographic image, as illustrated in the upper right image in FIG. 9B, an image not including a region with a parameter changed is displayed. In this manner, changing parameters through a touch operation is also applicable to three-dimensional ultrasound image data.

Changing parameters through a touch operation is also applicable to a VR image (the lower right image in FIG. 9A) by setting a certain algorithm in advance. For example, when a tap is made to specify a point (position) on the surface of a solid body, the position can be set even on a VR image. In this manner, changing parameters through a touch operation is also applicable to a VR image, using the processing described above. This example, describing a case of changing a parameter in a sphere region, is not limiting, and parameters can be changed in a cubic region, for example Other Embodiments In addition to the above-mentioned embodiments, various different embodiments may be implemented.

Combination of Touch Operations

For example, while the embodiments described above describes a case of individually performing various types of touch operations, such as a tap operation, a long-press operation, and a slide operation, these operations may be performed in combination as appropriate. For example, the operator can increase the gain with the length of time of a long-press operation and then performs tap operations for fine adjustment of the gain, thereby achieving a change in the gain depending on the number of times of tap operations. Parameters to be changed may vary for each touch operation. For example, the operator can change the gain with the length of time of a long-press operation, and change the dynamic range depending on the number of times of tap operations.

In a Case where No Medical Image is Displayed on Touch Panel

For example, the embodiments are applicable to touch panels with no medical image displayed thereon.

Figure 10:
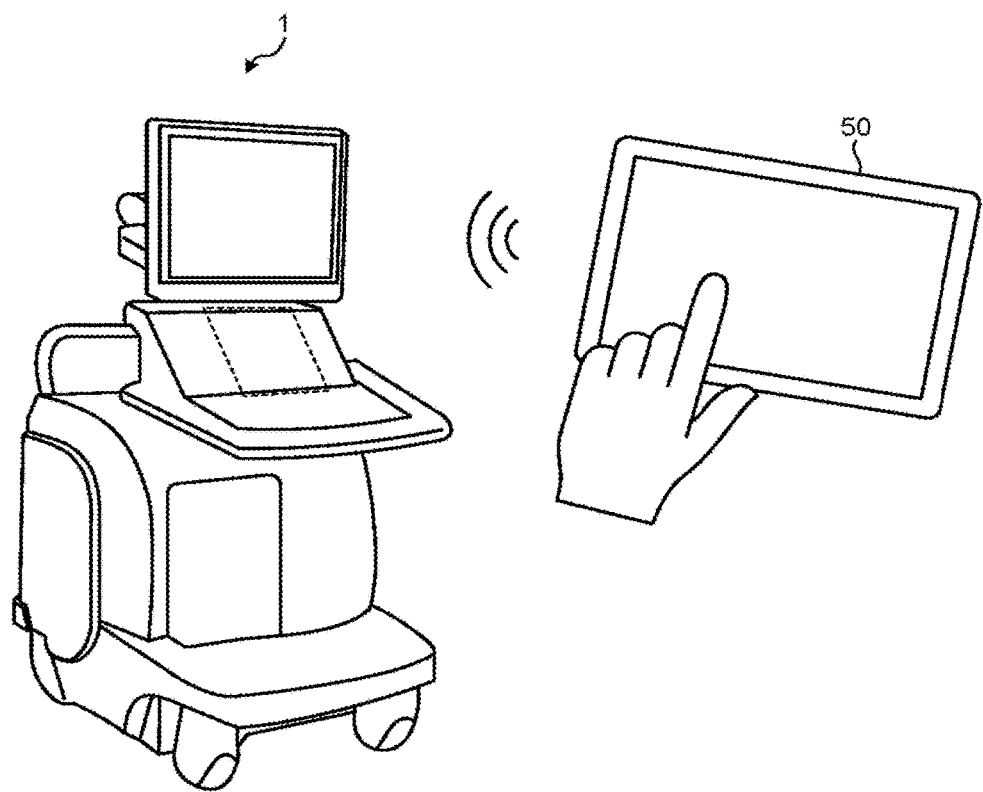
FIG. 10 is a diagram illustrating an example configuration of an ultrasound diagnostic apparatus according to another embodiment.

FIG. 10 is a diagram illustrating an example configuration of the ultrasound diagnostic apparatus 1 according to another embodiment. As illustrated in FIG. 10, touch panel 50 is disposed in an enclosure that is separate from the display 103 of the ultrasound diagnostic apparatus 1, includes a region with a positional relation associated with the medical image displayed by the display 103, and detects a touch operation on the region made by the operator. For example, while the touch panel 50 displays no medical image, its position on the display is associated with the position of the medical image on the display 103. The touch panel 50 then detects a touch operation made by the operator. Through this operation, the touch panel 50 can detect a touch operation on the medical image.

The control circuitry 170 changes a parameter that affects the display of the medical image in a region relative to a position in the medical image corresponding to the position where the touch operation is detected. For example, the control circuitry 170 changes a parameter based on the position on the display 103 corresponding to the position where the touch operation is detected on the touch panel 50.

Other Position Input Units

The ultrasound diagnostic apparatus 1 may use other position input units in changing parameters. Specifically, in the ultrasound diagnostic apparatus 1, the input device 102 receives a non-contact operation for specifying a position in a medical image. The control circuitry 170 then changes a parameter that affects the display of a medical image at least in a position specified by the non-contact operation.

Figure 11:
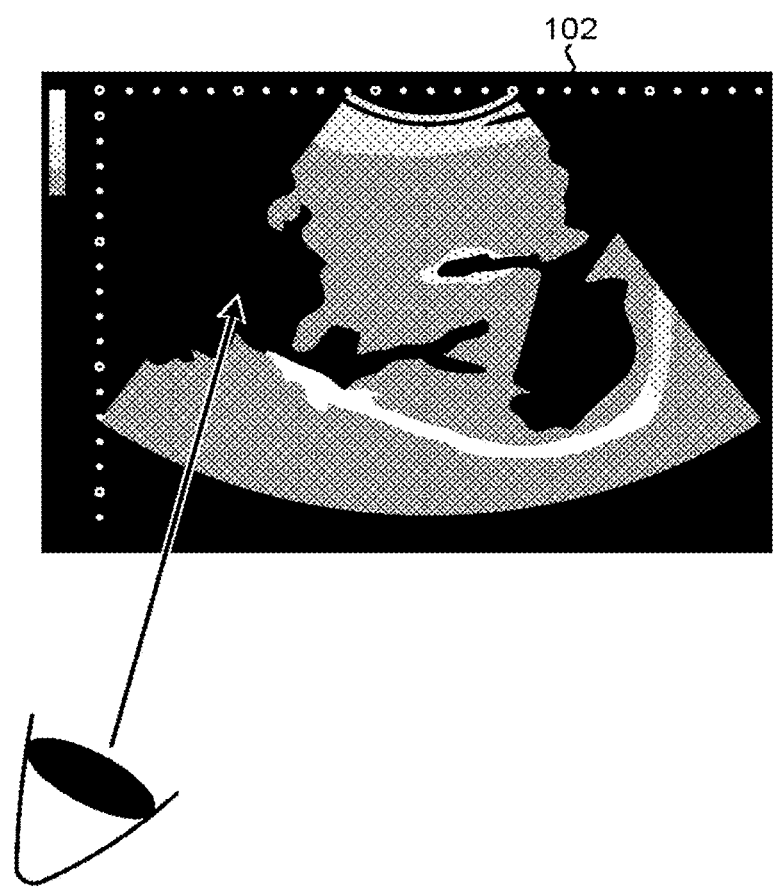
FIG. 11 is a diagram illustrating a position input module according to another embodiment.

FIG. 11 is a diagram illustrating a position input unit according to another embodiment. With reference to FIG. 11, input of a position made by the operator wearing a head mounted display (HMD) serving as the input device 102 is described. As illustrated in FIG. 11, the operator wearing the HMD can specify a position (coordinates) on a medical image by gazing at the position. After the position is detected, the control circuitry 170 can change a parameter in a region based on the position like in the above-described embodiments.

In addition, an input unit that uses virtual contact with a medical image projected in space is applicable as the input device 102. This is a unit for rendering an image on a position at which no visible things exist through imaging in space by employing a technology called space display or space projection, for example. By specifying a position on the image through a plurality of infrared sensors, for example, the input of the position can be achieved. For example, the operator can specify a position with his or her finger on a medical image projected in space. Positions that are specified individually are detected by a plurality of infrared sensors. The positions detected by the infrared sensors are converted into coordinates based on the positional relation with the image projected in space, whereby the positions can be detected as being specified in the medical image.

In addition, an audio input unit is applicable as the input device 102. In this case, audibly detectable keywords are associated in advance with positions (regions) on a medical image. For example, the medical image is divided into four sub-regions associated with keywords "upper right", "lower right", "upper left", and "lower left". With this configuration, for example, in response to an utterance "upper right" made by the operator, the audio input unit detects the keyword and converts the input into the corresponding region in the medical image. In this case, a parameter in the upper right region in the medical image will be changed.

Other Photographing Modes

A description is given of the case where the parameters are set in the B mode photographing in the embodiments described above, but embodiments are not limited to this. For example, the embodiments are also applicable to B mode, M mode, Doppler mode, color Doppler mode, power mode, tissue Doppler mode, and elastography mode, for example.

In this case, the control circuitry 170 changes the parameter that is any of gain, dynamic range, noise reduction filter level, and reception frequency when the medical image is generated in the B mode; changes the parameter that is any of M gain, M dynamic range, noise reduction filter level, edge enhancement level, and reception frequency when the medical image is generated in the M mode; changes the parameter that is any of Doppler gain, Doppler dynamic range, noise reduction filter level, and reception frequency when the medical image is generated in the Doppler mode; changes the parameter that is any of color gain, motion artifact reduction filter level, low-cut filter level, and reception frequency when the medical image is generated in the color Doppler mode; changes the parameter that is any of color gain, power dynamic range, low-cut filter level, and reception frequency when the medical image is generated in the power mode; changes the parameter that is any of color gain, motion artifact reduction filter level, and reception frequency when the medical image is generated in the tissue Doppler mode; and changes the parameter that is any of persistence level, reception frequency, and a mixed ratio of an elastography image to a mix-target image when the medical image is generated in the elastography mode. In the elastography mode, a semitransparent color image (stiffness image) is superimposed on a two-dimensional image. When a user touches an area around which he or she is going to observe, the transparency of the superimposed image is enhanced in the area around the touch position while the user keeps touching the area. This configuration can enhance the visibility of the two-dimensional image underlying the color image.

Flick Operation

A description is given of the case where a tap operation, a long-press operation, or the like is performed as an example of the touch operation in the embodiments described above, but embodiments are not limited to this. For example, a flick operation may be performed as the touch operation. The flick operation means, for example, an operation made by the operator quickly sliding his or her fingers on the display of the touch panel 104. In this case, the touch panel 104 can acquire information such as a position where the flick operation is detected (preferably a position that a finger touches first), the direction of the flick operation, and the speed of the flick operation. For example, the flick operation may be defined as an operation performed at or quicker than a predetermined speed and distinguished from operations performed at a speed below the predetermined speed (slide operation). Alternatively, the flick operation and the slide operation may be defined as the same operation.

In other words, the touch panel 104 displays a medical image, and detects a flick operation on the displayed medical image. The control unit 170 changes a parameter that affects the display of the medical image in a region relative to a position where the flick operation is detected, based on at least one of the direction of the flick operation and the speed of the flick operation.

Figure 12:
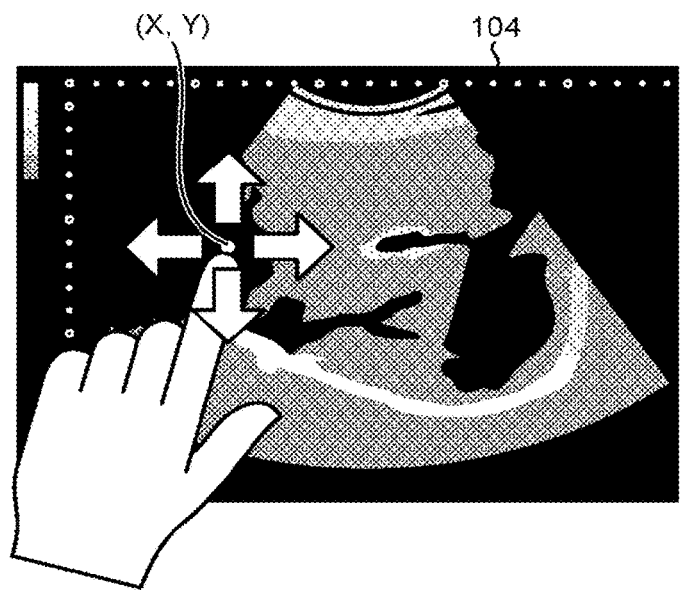
FIG. 12 illustrates processing of a touch panel according to another embodiment.

FIG. 12 is a diagram illustrating processing of a touch panel according to another embodiment. FIG. 4 illustrates the touch panel 104 on which an ultrasound image is displayed. As illustrated in FIG. 4, the touch panel 104 detects flick operations in the upward direction, the downward direction, the rightward direction, the leftward direction at the coordinates (X, Y) on the ultrasound image. In FIG. 12, the control unit 170 changes a parameter in a certain region having the coordinates (X, Y) at its center.

The control unit 170 determines the type of the parameter to be changed and whether to increase or decrease the parameter depending on the direction of a flick operation detected by the touch panel 104. For example, when the touch panel 104 receives a flick operation in the upward direction, the control unit 170 determines the type of the parameter to be "gain" and the parameter to "increase". In other words, in response to a flick operation in the upward direction made by the operator, the control unit 170 determines an increase in the gain of the ultrasound image. For example, when the touch panel 104 receives a flick operation in the downward direction, the control unit 170 determines the type of the parameter to be "gain" and the parameter to "decrease". In other words, in response to a flick operation in the downward direction made by the operator, the control unit 170 determines a decrease in the gain of the ultrasound image. For example, when the touch panel 104 receives a flick operation in the rightward direction, the control unit 170 determines the type of the parameter to be "dynamic range" and the parameter to "increase". In other words, in response to a flick operation in the rightward direction made by the operator, the control unit 170 determines an increase in the dynamic range of the ultrasound image. For example, when the touch panel 104 receives a flick operation in the leftward direction, the control unit 170 determines the type of the parameter to be "dynamic range" and the parameter to "decrease". In other words, in response to a flick operation in the leftward direction made by the operator, the control unit 170 determines a decrease in the dynamic range of the ultrasound image.

The control unit 170 determines the variation of the parameter to be changed depending on the speed of a flick operation detected by the touch panel 104. As an example, the control unit 170 determines a larger change (increase or decrease) in the parameter in response to a quicker flick operation.

In this manner, the control unit 170 changes the parameter depending on the direction and the speed of a flick operation detected by the touch panel 104.

Note that FIG. 12 is only illustrative. For example, the types of parameters and whether to increase or decrease the parameters determined depending on the directions of flick operations are not limited to the examples described above. Specifically, the types of parameters to be changed may be any desired parameters described above, such as edge enhancement level and reception frequency. In addition, a parameter may be decreased through a flick operation in the upward direction. When the touch panel 104 detects a flick operation in a diagonal direction, the type of parameter corresponding to this direction may be changed.

Detection of Strong Press

When the touch panel 104 is capable of detecting the strength of a touch operation, the control unit 170 may change a parameter based on the strength of the touch operation.

For example, a touch panel 104 including both a capacitance detection mechanism and a pressure-sensitive detection mechanism can detect the strength of a touch operation. In this case, the touch panel 104 includes the capacitance detection mechanism on the outer side on which the operator can touch and includes the pressure-sensitive detection mechanism on the inner side of the capacitance detection mechanism. In this example, the capacitance detection mechanism can detect information such as a position (coordinates) at which the operator touches through a touch operation, the length of time during which the operator has touched the position, and the number of times of touching. By contrast, the pressure-sensitive detection mechanism can detect a touch operation of a predetermined strength or larger (also referred to as "strong press" or "deep press"). The pressure-sensitive detection mechanism includes, for example, a glass plate that curves under a pressure of a predetermined strength or larger, and can detect the curving of the glass plate, thereby detecting whether a touch operation is strong press.

In this case, the control unit 170 determines the type of the parameter to be changed and whether to increase or decrease the parameter every time a tap operation, a long-press operation, or a flick operation of a predetermined strength or larger is detected.

For example, patterns for the type of the parameter and whether to increase or decrease the parameter are set in advance, and the control unit 170 switches one pattern to another every time strong press is detected.

As an example, a first pattern "to increase the gain", a second pattern "to decrease the gain", a third pattern "to increase the dynamic range", and a fourth pattern "to decrease the dynamic range" are set in advance. The control unit 170 sequentially switches one pattern to another between the first pattern to the fourth pattern depending on the number of times of strong press.

Specifically, when receiving no strong press (tap operation), the control unit 170 presets the first pattern. In this case, when the touch panel 104 detects tap operations, the control unit 170 increases the gain depending on the position and the number of times of tap operations.

When the touch panel 104 detects strong press one time, the control unit 170 switches the first pattern to the second pattern. When the touch panel 104 detects tap operations in the state in which the second pattern has been set, the control unit 170 decreases the gain depending on the position and the number of times of tap operations.

When the touch panel 104 detects strong press one time thereafter (in other words, strong press has been detected a total of two times from the preset state), the control unit 170 switches the second pattern to the third pattern. When the touch panel 104 detects tap operations in the state in which the third pattern has been set, the control unit 170 increases the dynamic range depending on the position and the number of times of tap operations.

Furthermore, when the touch panel 104 detects strong press one time thereafter (in other words, strong press has been detected a total of three times from the preset state), the control unit 170 switches the third pattern to the fourth pattern. When the touch panel 104 detects tap operations in the state in which the fourth pattern has been set, the control unit 170 decreases the dynamic range depending on the position and the number of times of tap operations.

In this manner, the control unit 170 determines the type of the parameter to be changed and whether to increase or decrease the parameter every time strong press is detected. While a description is given of the case where strong press of a tap operation in the example described above, strong press of a long-press operation or strong press of a flick operation can also be detected to adjust the parameter depending on the detected operation. Specifically, the control unit 170 determines the type of the parameter to be changed and whether to increase or decrease the parameter every time a tap operation, a long-press operation, or a flick operation of a predetermined strength or larger is detected.

Combinations

The embodiments described above may be implemented in combination as appropriate. Specifically, the touch panel 104 displays a medical image and detects a tap operation, a long-press operation, or a flick operation on the displayed medical image. The control unit 170 changes a parameter that affects the display of the medical image in a region relative to a position where the tap operation, the long-press operation, or the flick operation is detected, based on at least one of the strength of the tap operation, the number of times of the tap operation, the strength of the long-press operation, the long-press time of the long-press operation, the strength of the flick operation, the direction of the flick operation, and the speed of the flick operation.

Medical Imaging Apparatus

The processing described in the embodiments described above may be executed in a medical imaging apparatus. The medical imaging apparatus described below may be configured as an image display apparatus.

Figure 13:
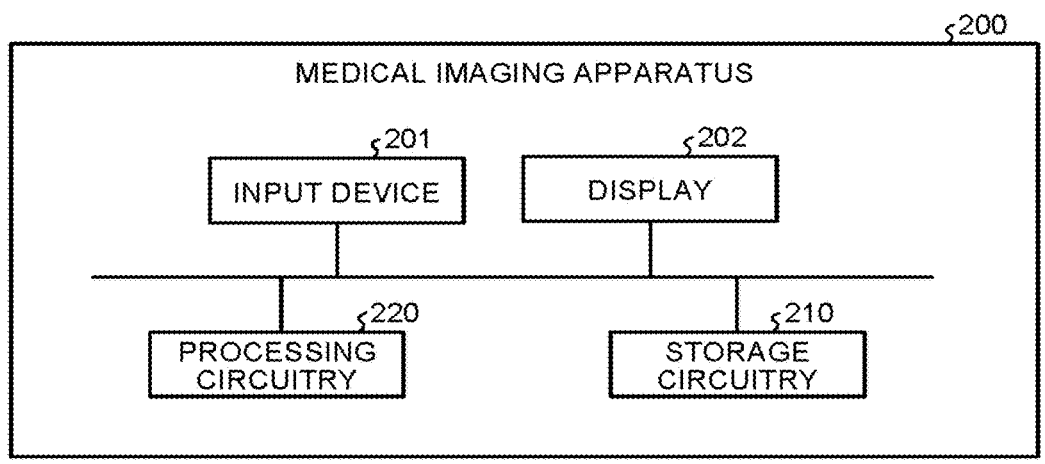
FIG. 13 is a block diagram illustrating an example configuration of a medical imaging apparatus according to another embodiment.

FIG. 13 is a block diagram illustrating an example configuration of a medical imaging apparatus according to another embodiment. As illustrated in FIG. 13, a medical imaging apparatus 200 includes an input device 201, a display 202, storage circuitry 210, and processing circuitry 220.

Examples of the input device 201 include a mouse, a keyboard, a button, a panel switch, a touch command screen, a foot switch, a trackball, and a joystick. The input device 201 receives various kinds of setting requests from an operator of the medical imaging apparatus 200, and transfers the various kinds of received setting requests to the processing units.

The display 202 displays a GUI used by the operator of the medical imaging apparatus 200 to input various kinds of setting requests with the input device 201, and displays information generated by the medical imaging apparatus 200 and other data.

The storage circuitry 210 is a non-volatile storage device such as a flash memory and other semiconductor memory devices, a hard disk, and an optical disc.

The processing circuitry 220 is an integrated circuit such as an ASIC and an FPGA or an electronic circuit such as a CPU or a micro processing circuit (MPU), and controls the entire processing of the medical imaging apparatus 200.

Specifically, the input device 201 functioning as a touch panel displays a medical image generated based on scanning on a subject and detects a touch operation on the displayed medical image. The processing circuitry 220 functioning as a control unit changes a parameter that affects the display of the medical image in a region relative to a position where the touch operation is detected.

Furthermore, each component of each device is conceptually illustrated based on its function, and is not necessarily required to be physically configured as illustrated. In other words, a specific mode for dispersion and integration of the devices is not limited to the illustrated one, and all or part of the devices can be functionally or physically dispersed and integrated in arbitrary units depending on various kinds of loads, usage conditions, and other parameter. In addition, all or any part of each processing function executed by each device may be implemented by a CPU and a computer program analyzed and executed by the CPU, or implemented as hardware by wired logic.

Furthermore, among the processing contents described in the above-mentioned embodiments, all or part of the processing that is described as being automatically executed can also be manually executed, or all or part of the processing that is described as being manually executed can also be automatically executed by a known method. In addition, the processing procedures, the control procedures, the specific names, and the information including various kinds of data and parameter described herein and illustrated in the accompanying drawings can be arbitrarily changed unless otherwise specified.

Furthermore, the medical imaging method described in the above-mentioned embodiment can be implemented by a computer such as a personal computer or a workstation executing a medical imaging program prepared in advance. The medical imaging method can be distributed via a network such as the Internet. Furthermore, the medical imaging method can be recorded in a computer-readable recording medium, such as a hard disk, a flexible disk (FD), a CD-ROM, an MO, and a DVD, and executed by a computer reading the method from the recording medium.

According to at least one of the embodiments described above, the image quality of a desired region can be easily changed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnostic apparatus comprising:
image generation circuitry configured to generate a medical image based on data collected through scanning on a subject;
a touch panel configured to display the medical image, and detect a tap operation, a long-press operation, or a flick operation on the displayed medical image; and
control circuitry configured to change a parameter that affects display of the medical image in a region relative to a position where the tap operation, the long-press operation, or the flick operation is detected, based on a touch operation corresponding to at least one of strength of the tap operation, number of times of the tap operation, strength of the long-press operation, a long-press time of the long-press operation, strength of the flick operation, a direction of the flick operation, and speed of the flick operation,
wherein the control circuitry:
changes, based on the touch operation, the parameter that is any of gain, dynamic range, noise reduction filter level, and reception frequency when the medical image is generated in B mode,
changes, based on the touch operation, the parameter that is any of M gain, M dynamic range, noise reduction filter level, edge enhancement level, and reception frequency when the medical image is generated in M mode,
changes, based on the touch operation, the parameter that is any of Doppler gain, Doppler dynamic range, noise reduction filter level, and reception frequency when the medical image is generated in Doppler mode,
changes, based on the touch operation, the parameter that is any of color gain, motion artifact reduction filter level, low-cut filter level, and reception frequency when the medical image is generated in color Doppler mode,
changes, based on the touch operation, the parameter that is any of color gain, power dynamic range, low-cut filter level, and reception frequency when the medical image is generated in power mode,
changes, based on the touch operation, the parameter that is any of color gain, motion artifact reduction filter level, and reception frequency when the medical image is generated in tissue Doppler mode, and changes, based on the touch operation, the parameter that is any of persistence level, reception frequency, and a mixed ratio of an elastography image to a mix-target image when the medical image is generated in elastography mode.

2. The medical image diagnostic apparatus according to claim 1, wherein the control circuitry changes the parameter in the region that is a square region, a cubic region, a circle region, or a sphere region including the position where the tap operation, the long-press operation, or the flick operation is detected.

3. The medical image diagnostic apparatus according to claim 1, wherein
   the touch panel further displays a graphic for allowing a determination on whether to increase or decrease the parameter, and detects the tap operation, the long-press operation, or the flick operation on the displayed graphic, and
   the control circuitry changes setting on whether to increase or decrease the parameter based on a tap operation, a long-press operation, or a flick operation on the medical image, depending on the tap operation, the long-press operation, or the flick operation detected on the graphic.

4. The medical image diagnostic apparatus according to claim 1, wherein the control circuitry determines a type of the parameter to be changed and whether to increase or decrease the parameter depending on a direction of the flick operation detected by the touch panel.

5. The medical image diagnostic apparatus according to claim 1, wherein the control circuitry determines a type of the parameter to be changed and whether to increase or decrease the parameter every time the tap operation, the long-press operation, or the flick operation of a predetermined strength or larger is detected.

6. The medical image diagnostic apparatus according to claim 1, wherein the control circuitry determines a variation of the parameter depending on the number of times of the tap operation, the long-press time of the long-press operation, or the speed of the flick operation detected by the touch panel.

7. A medical image diagnostic apparatus comprising:
   image generation circuitry configured to generate a medical image based on data collected through scanning on a subject;
   a display configured to display the medical image;
   a touch panel disposed in an enclosure that is separate from the display and including a region with a positional relation associated with the medical image, the touch panel being configured to detect a touch operation on the region made by the operator; and
   control circuitry configured to change, based on the touch operation, a parameter that affects display of the medical image in a region relative to a position in the medical image corresponding to a position where the touch operation is detected,
   wherein the control circuitry:
      changes, based on the touch operation, the parameter that is any of gain, dynamic range, noise reduction filter level, and reception frequency when the medical image is generated in B mode,
      changes, based on the touch operation, the parameter that is any of M gain, M dynamic range, noise reduction filter level, edge enhancement level, and reception frequency when the medical image is generated in M mode,
      changes, based on the touch operation, the parameter that is any of Doppler gain, Doppler dynamic range, noise reduction filter level, and reception frequency when the medical image is generated in Doppler mode,
      changes, based on the touch operation, the parameter that is any of color gain, motion artifact reduction filter level, low-cut filter level, and reception frequency when the medical image is generated in color Doppler mode,
      changes, based on the touch operation, the parameter that is any of color gain, power dynamic range, low-cut filter level, and reception frequency when the medical image is generated in power mode,
      changes, based on the touch operation, the parameter that is any of color gain, motion artifact reduction filter level, and reception frequency when the medical image is generated in tissue Doppler mode, and
      changes, based on the touch operation, the parameter that is any of persistence level, reception frequency, and a mixed ratio of an elastography image to a mix-target image when the medical image is generated in elastography mode.

* * * * *